United States Patent [19]

Yamada et al.

[11] Patent Number: 4,925,730

[45] Date of Patent: May 15, 1990

[54] LIQUID ACTIVE SUBSTANCE SLOW RELEASING DEVICE

[75] Inventors: Shinji Yamada; Yutaka Aoki, both of Osaka, Japan

[73] Assignee: Nitto Denko Corporation, Osaka, Japan

[21] Appl. No.: 269,337

[22] Filed: Nov. 10, 1988

[30] Foreign Application Priority Data

Nov. 12, 1987 [JP] Japan ................................. 62-286788

[51] Int. Cl.$^5$ ........................ G01N 21/17; B32B 3/26
[52] U.S. Cl. .................................. 428/305.5; 116/200;
424/7.1; 428/315.5; 428/315.9; 428/319.1;
428/319.3; 428/905; 428/907
[58] Field of Search .................... 428/905, 907, 305.5,
428/319.1, 319.3, 315.5, 315.7, 315.9; 424/7.1;
523/102; 116/200

[56] References Cited

U.S. PATENT DOCUMENTS

| | | | |
|---|---|---|---|
| 3,784,488 | 1/1974 | Steinhauer et al. | 524/379 X |
| 4,017,030 | 4/1977 | Coplan et al. | 239/44 |
| 4,051,159 | 9/1977 | Tsoucalos et al. | 523/102 X |
| 4,138,344 | 2/1979 | Choi et al. | 424/426 X |
| 4,279,213 | 7/1981 | Urahama et al. | |
| 4,286,020 | 8/1981 | Himel et al. | 428/407 |
| 4,734,278 | 3/1988 | Pougalan et al. | 523/102 X |
| 4,735,972 | 4/1988 | Shigematsu et al. | 523/102 |

FOREIGN PATENT DOCUMENTS 57-31067 7/1982 Japan .
59-59733 4/1984 Japan .

OTHER PUBLICATIONS

European Search Report, EP 88 11 8762.

*Primary Examiner*—William J. Van Balen
*Attorney, Agent, or Firm*—Sughrue, Mion, Zinn, Macpeak & Seas

[57] ABSTRACT

A liquid active substance slow releasing device comprising a thermoplastic polyester resin having a glass transition point of from 5° C. to 80° C. and an evaporative liquid active substance having a limited solubility for the aforesaid thermoplastic resin, said device being an opaque resin molding of the thermoplastic resin having dispersed therein the liquid active substance as fine droplets in an amount over the saturation solubility and becoming substantially transparent when the amount of the liquid active substance in the resin molding is reduced.

4 Claims, 3 Drawing Sheets

LIQUID ACTIVE SUBSTANCE SLOW RELEASING DEVICE

FIELD OF THE INVENTION

This invention relates a liquid active substance slow releasing device capable of releasing as vapor a liquid active substance at a substantially constant controlled rate for a long period of time and also visually confirming the substantial termination of the release of the liquid active substance.

BACKGROUND OF THE INVENTION

For releasing an active substance into the surrounding atmosphere under a controlled condition, various kinds of slow releasing devices are known For example, there are devices encapsulating an active substance in microcapsules as described in U.S. Pat. Nos. 4,286,020 and 4,353,962 and devices enclosing an active substance in tubes or capillaries as described in JP-A-52-55969 and 57-45101 (the term "JP-A" as used herein means an "unexamined published Japanese patent application), and U.S. Pat. No. 4,017,030. Furthermore, there is also proposed a device of impregnating a porous regin molding having continuous perforations with an active substance as described in JP-A-59-13701. U.S. Pat. No. 3,784,488 discloses a film forming solution composition. The composition is prepared by dispersing an excess of oil components into a soft polymer structure, and is applied to a skin of human body to form a film, thereby maintaining the effect of a sunscreen oil. U.S. Pat. No. 4,138,344 discloses a device wherein a solid active substance is despersed in a polymer matrix which is decomposable in a living body, and as the polymer dissolves, the active substance gradually releases.

However, in such active substance slow releasing devices, an active substance is generally released for a long period of time and after passing a period capable of effectively releasing the active substance, the releasing rate of the active substance is reduced and finally the activity thereof is vanished but it has hitherto been difficult to clearly confirm the diminished effect of the active substance.

Furthermore, since the releasing rate of an active substance from such a slow releasing device greatly deviates according to the surrounding atmospheric conditions such as temperature, humidity, etc., and the period of effectively releasing the active substance, that is, the life of the active substance is not always constant, the effective period indicated on the device is a simple prospective criterion and is not a highly reliable term. Accordingly, conventional slow releasing devices are frequently still used even vanishing the activity of the active substance or they are frequently discarded as activity vanished devices in spite of that they still retain the activity.

For solving the aforesaid problems in conventional active substance slow releasing device, a device wherein a solid active substance is dispersed as fine solid particles in a substantially transparent and inactive resin in an amount of more than the saturated solubility is proposed as described in JP-B-U-57-31067 (the term "JP-B-U" as used herein means an "examined published Japanese untility model application"). According to the device, since the device is opaque when a sufficient amount of the active substance exists in the molding in a sufficient amount but the resin molding becomes substantially transparent when the greater part of the active substance is evaporated or dissolved off from the molding and the existing amount thereof in the resin molding reaches the saturated solubility, the vanishment of the acitivity of the device can be visually confirmed.

On the other hand, as a device for slow releasing an active material which is liquid at normal temperature, there is proposed a device of enclosing a liquid active material having a limited solubility for a polymer in a layer of the polymer in an amount of the solubility as independent fine droplets as described in JP-A-59-59733, However, in such a device, since the polyer molding or layer retains the independent fine pores and has the porous structure after releasing the liquid active substance different from the aforesaid case that the active substance is solid, the device does not become transparent and is opaque, thereby the vanishment of the active substance can not visually confirm.

SUMMARY OF THE INVENTION

As the result of various investigations for solving the aforesaid problem in the device for slow releasing a liquid active substance, in particular the problem of confirming or indicating the vanishment of the activity of a liquid active substance, the inventors have discovered that when a thermoplastic polyester resin having a definite glass transition point is used as a matrix or a carrier for a liquid active substance, the resin molding becomes unexpectedly substantially transparent and thus a device capable of visually conforming the vanishment of the activity can be obtained and have succeeded in attaining the present invention based on the discovery.

Thus, according to this invention, there is provided a liquid active substance slow releasing device comprising a thermoplastic polyester resin having a glass transition point of 5° C. to 80° C. and an evaporative liquid active substance having a limited solubility for the aforesaid thermoplastic resin, said device being an opaque resin molding of the thermoplastic resin having dispersed therein the liquid active substance as fine droplets in an amount over the saturated solubility and becoming substantially transparent when the amount of the liquid active substance in the resin molding is reduced.

DETAILED DESCRIPTION OF THE INVENTION

Figure 1:
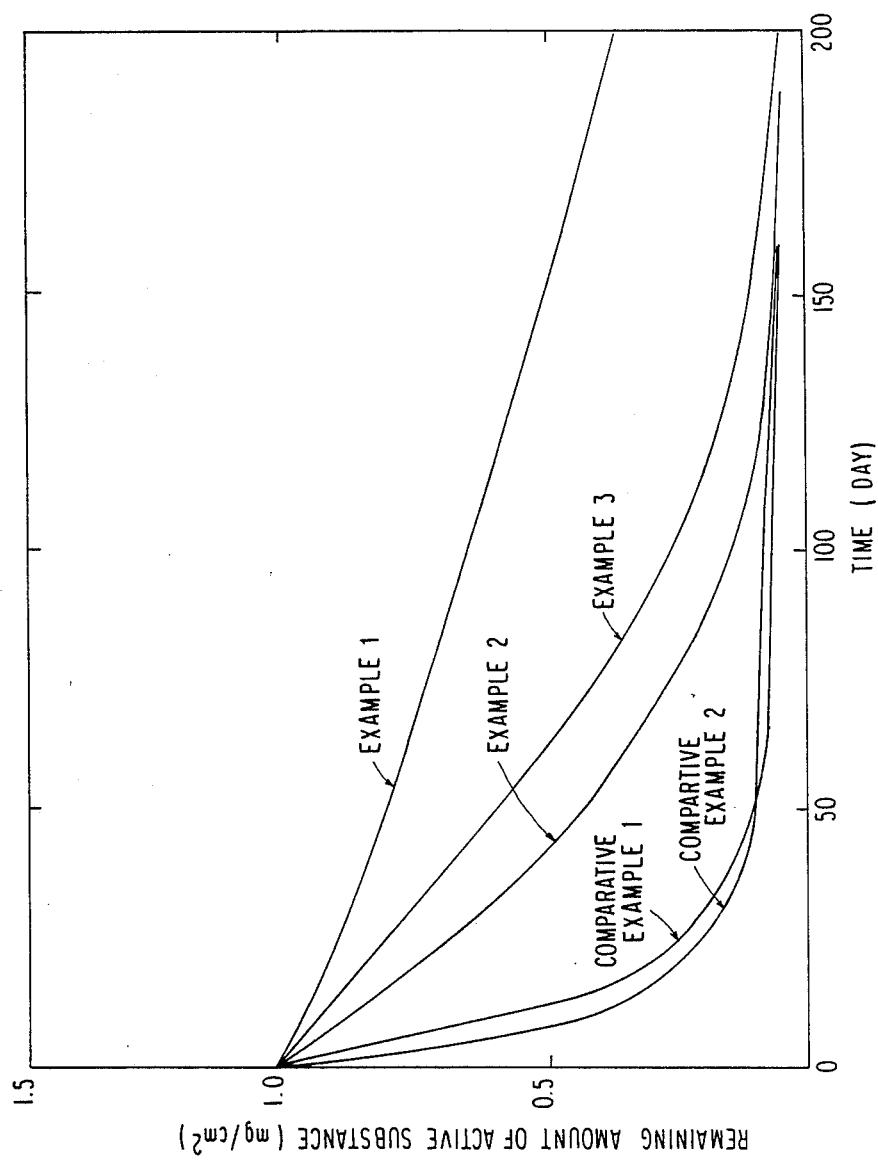
FIG. 1 is a graph showing the remaining amounts of active substance in the liquid active substance slow releasing devices of this invention and the liquid active substance slow releasing devices in comparison examples in the case of allowing to stand these devices at normal temperature.

In this invention, the term "liquid active substance" means a substance which is a liquid at normal temperature and evaporates into surrounding atmosphere to show chemical or physiological activity such as attractant activity, pesticidal activity, repellent activity, and aromatic acitivity. Practical examples thereof are attractant active substances such as Z-11-tetradecenyl acetate, Z-9-tetradecenyl acetate, E-11-tetradecenyl acetate, Z-9-dodecenyl acetate, 10-methyldodecyl acetate, Z-13-octadecenal, Z-11-hexadecenal, E-11-hexadecenal, Z-9-hexadecenal, etc.; pesticidal active substances such as Naled, Diazinon, Sumithion, pyrethroido series compounds, etc. (insectcides) and also β-propiolactone, etc. (pesticides); repellent active substances such as triethylene glycol monohexyl ether, N,N-diethyl-m-toluamide, etc.; and aromatic active substances such as farnesol, farnesene, limonene, benzyl alcohol, and esters, ethers, and aldehydes induced from hydrocarbons having from 6 to 16 carbon atoms.

In the liquid active substance slow releasing device of this invention, as the resin constituting the matrix or the carrier thereof, a thermoplastic polyester resin having a glass transition point of from 5° C. to 80° C., and particularly from 40° C. to 80° C. is used. If the glass transition point of a thermoplastic polyester resin is lower than 5° C., an active substance is released from the resin molding in a short period of time, whereby it is impossible to releasing the active substance over a long period of time as well as although the reason has not yet been clarified, the resin molding having dispersed therein a liquid active substance as fine droplets is always transparent regardless of the amount of the active substance dispersed in the resin.

On the other hand, by using a thermoplastic polyester resin having a glass transition point of from 5° C. to 80° C. as the matric or the carrier according to this invention, the resin molding changes from opaque to substantial transparent when the concentration of the active substance in the molding reaches about the saturation solubility and hence by the change into transparence, the vanishment of the activity of the slow releasing device can be visually perceived or confirmed.

The reason that by using the thermoplastic polyester resin having a glass transition point of from 5° C. to 80° C. as the matric or the carrier, the resin molding becomes substantially transparent when the amount of the active substance contained in the resin molding is reduced has not yet been clarified but as a phenomenon, it has been confirmed that with the dissolution of the liquid active substance dispersed in the resin as liquid droplets into the resin, the active substance passes through the resin and is released into the surrounding atmosphere, whereby the size of the independent fine pores containing the liquid droplets is reduced following the release of the liquid droplets to provide the homogeneous resin molding containing no fine pores.

In the case of using a conventional resin which is used as a matrix or carrier for such a slow releasing device, e.g., the polysulfon resin described in JP-A-59-59733, the resin has a high glass transition point and when the amount of an active substance dispersed in the resin molding as fine liquid droplets is reduced and reaches almost the saturation solubility for the resin, the resin can not follow the reduction of the liquid droplets and retains the porous structure having initial fine pores, whereby the resin molding remain as opaque molding.

Furthermore, in this invention, it is necessary that the thermoplastic polyester resin has a limited solubility for the liquid active substance. That is, it is preferred that the resin dissolves the liquid active substance in the range of less than 20 parts by weight only, in particular in the range of from 0.001 to 5 parts by weight for 100 parts by weight of the resin.

When the form of the device of this invention is a sheet or film, the device is produced by dissolving the aforesaid thermoplastic polyester resin and the active substant which is liquid at normal temperature in an organic solvent which can dissolve both the resin and the active substance and is more easily volatile than the active substance, coating the solution on a proper support, and evaporating the solvent to form a resin molding (resin layer) uniformly having many independent fine pores and also enclose the liquid active substance in the fine pores as liquid droplets. It is preferred that the device of this invention is in the form of thin sheet or film for clearly perceive the vanishment of the activity by the change of the molding into transparence.

Furthermore, the device of this invention in the form of block, sheet or film can be produced by kneading the aforesaid thermoplastic polyester resin and the active substance which is liquid at normal temperature with an organic solvent which can dissolve both the resin and the active substance and is more easily volatile than the active substance, molding the kneaded mixture into a block, sheet or film, and evaporating the solvent to form a resin molding uniformly having many independent fine pores and enclose the liquid active substance in the fine pores as liquid droplets.

In the aforesaid method, the aforesaid liquid active substance is used in an amount of over the saturation solubility for the resin being used so that the active substance is released in the surrounding atmosphere from the resin molding obtained at a substantially definite rate and can be dispersed in the resin as fine liquid droplets.

The aforesaid organic solvent is required to have properties capable of dissolving both the liquid active substance and the thermoplastic polyester resin being used and of more easily volatile than the liquid active substance, and also is required to have low boiling point. The organic solvent is properly selected according to the active substance being used. Specific examples of the organic solvent are aromatic hydrocarbons such as benzene, toluene, xylene, etc.; halogenated lower aliphatic hydrocarbons such as methylene chloride, chloroform, tolycrene, propylene dichloride, etc.; lower dialkyl ketones such as acetone, methyl ethyl ketone, methyl isobutyl ketone, etc.; esters such as methyl acetate, ethyl acetate, butyl acetate, cellosolve acetate, etc.; cyclohexanone, dioxane, and tetrahydrofuran. They may be used as a mixture thereof.

The temperature for evaporating the organic solvent is usually from 0° C. to 100° C., preferably in the range of from 15° C. to 70° C., and is lower than the boiling point of the solvent. Thus, the evaporation of the solvent may be usually performed at normal temperature but, if necessary, may be performed at by heating to a temperature of lower than the boiling point of the solvent. Also, the organic solvent may be evaporated under reduced pressure.

Since the liquid active substance has a limited solubility for the thermoplatic polyester resin and is incorporated in the resin in an amount of over the saturation solubility for the resin, a phase separation occurs between the active substance and the resin with the evaporation of the organic solvent, and the fine liquid droplets of the active substance are uniformly dispersed in the resin matrix, whereby the resin forms a porous material having many independent fine pores and the liquid active substance is enclosed in the fine pores as fine liquid droplets.

The liquid active substance slow releasing device of this invention thus obtained has many independent fine pores having pore sizes of usually from 0.1 μm to 5 μm and the fine pores are insulated from each other by thin walls having a thickness of from 0.1 μm to 5 μm. The liquid active substance is enclosed in the fine pores and thus dispersed in the resin layer or molding.

There is no particular restriction on the thickness of the resin layer or resin molding if it becomes transparent after releasing the liquid active substance but as described above, the resin layer or molding is preferably in the form of thin sheet or film and is particularly preferably a thin sheet or film having a thickness of from 10 μm to 500 μm. Furthermore, the voids thereof are usually from about 30% to 80%. Accordingly, in the device of this invention, the resin layer or molding has very large voids and thus can contain a liquid active substance upto about 70% by weight. However, practically, about 50% by weight is a proper maximum content.

In the device of this invention, a sheet for inhibiting the active substance from permeating, i.e., a backing is usually formed at the back surface of the resin layer or molding. As such a backing, a foil or thin sheet of a metal such as aluminum, etc., a thin sheet or film of a resin such as polyethylene terephthalate, polyethylene, polypropylene, polyvinyl chloride, etc., a resin film having a metal vapor-deposited layer, a paper laminated with a metal foil, a resin film laminated with a metal foil, etc., are used.

Furthermore, in the device of this invention, a message such as "END", etc., exists between the resin layer or molding and the backing, such a message can be read when the molding becomes transparent, whereby the vanishment of the activity of the device can be more clearly perceived. Such a message may be printed on the backing. With or without the message, the backing may be colored.

Furthermore, if necessary, a control layer composed of a polymer film may be formed on the surface of the layer as the carrier for controlling the release of the active substance from the carrier. Examples of the polymer for the control layer are preferably polyethylene films, polypropylene films, and polyethylene terephthalate films.

As described above, the liquid active substance slow releasing device of this invention is composed of a thermoplastic polyester resin having the limited glass transition point as the matrix or the carrier thereof and a liquid active substance having very low solubility therefor dispersed in the resin may independent fine liquid droplets in an amount over the saturation solubility thereof. Thus, in the device of this invention, the diffusion of the liquid active substance in the fine pores into the carrier resin is greatly controlled and thus the active substance is released in the surrounding atmosphere at a substantially constant-controlled rate for a very long period of time.

Furthermore, in the device of this invention, the resin molding or layer becomes substantially transparent when the amount of the active substance in the resin reaches almost the saturation solubility in spite of that the active substance is liquid, and hence the vanishment of the activity of the device can be clearly visually perceived or confirmed.

Moreover, in the device of this invention, the fine pores of the porous carrier layer or molding are independent from each other different from a conventional device composed of a porous material having perforations simply impregnated with a liquid active substance, and hence the device can cut into desired dimensions or forms. Also, the device of this invention has flexibility and hence the form can be freely changed according to the purpose.

Then, the following examples are intended to illustrate more practically the present invention but not to limit it any way.

EXAMPLE 1

After dissolving 5 g of a thermoplastic polyester resin (Vylon 200, trade name, made by Toyobo Co., Ltd., glass transition point 67° C. by a differential thermal analysis) in 30 ml of methylene chloride, 1 g of an insect attractor, Z-11-tetradecenyl acetate was dissolved therein to provide a homogeneous solution.

The solution was coated on a polyethylene terephthalate film having vapor-deposited aluminum layer at a thickness of 500 μm at room temperature and allowed to evaporated methylene chloride at 40° C. to provide a liquid slow releasing device of this invention containing about 15% by weight of the attractant and having a thickness of about 70 μm.

The decice was allowed to stand in an open atmosphere at 30° C. and the remaining amount of the active substance in the device was measured by gas chromatography. The results obtained are shown in FIG. 1. Also, the change in transparency of the device with the passage of time is shown in Table 1 below.

Figure 2:
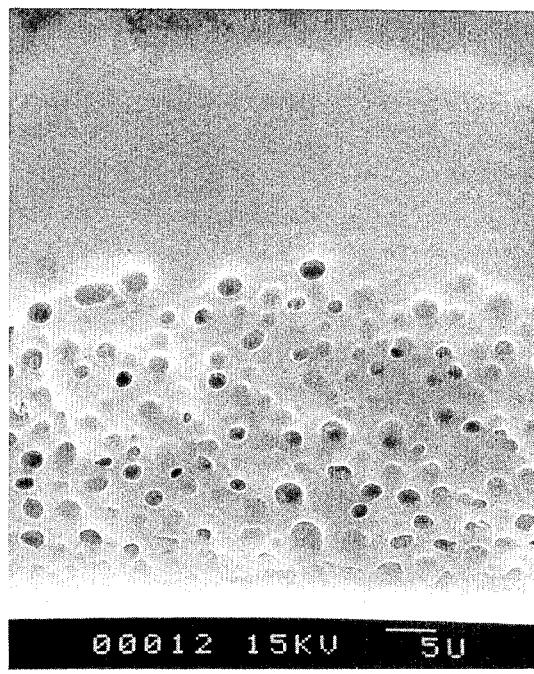
FIG. 2 is an electron micrograph (magnification:×2,000) showing the change of the state of the cross section of the device of this invention in the thickness direction of the resin layer directly preparation thereof with the passage of time.
Figure 3:
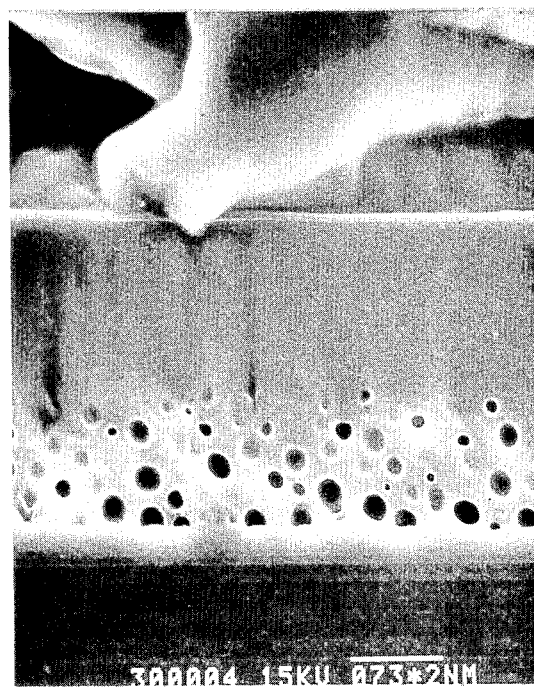
FIG. 3 is an electron micrograph showing the state as above after 3 months since the preparation thereof.
Figure 4:
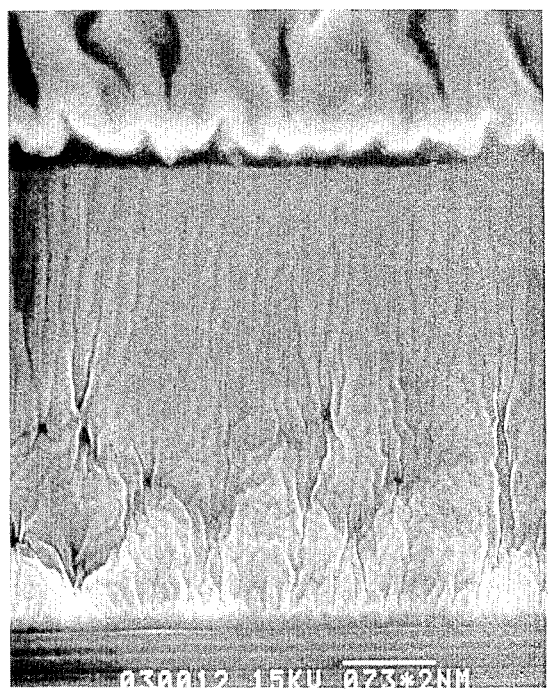
FIG. 4 is an electron micrograph showing the state as above after 10 months since the preparation thereof.

The change of the cross section of the resin layer in the thickness direction after the preparation of the device with the passage of time is shown in from FIG. 2 to FIG. 4 by electron micrographs (magnification ×2,000). FIG. 2 shows the cross section directly after the preparation of the device, which clearly shows the porous structure of the resin layer. FIG. 3 shows the cross section of the device after 3 months, which shows vanishing of the porous structure in the portion layer of the resin layer. FIG. 4 shows the cross section after 10 months, which shows the vanishing of the initial porous structure in the thickness direction of the resin layer and the formation of almost homogeneous structure.

EXAMPLE 2

After dissolving 5 g of a thermoplastic polyester resin (Polyester TP-217, trade name, made by The Nippon Synthetic Chemical Industry Co., Ltd., glass transition point 40° C.) in 30 ml of methylene chloride, 1 g of Z-11-tetradecenyl acetate was dissolved therein to provide a homogeneous solution.

The solution was coated on a polyethylene terephthalate film at a thickness of 500 μm at room temperature and allowed to evaporate methylene chloride at 40° C. to provide a liquid active substance slow releasing device of this invention containing about 15% by weight the attractant and having a thickness of about 70 μm.

The device was allowed to stand in an open atmosphere at 30° C. and then the remaining amount of the active subtance in the device was measured from the weight loss. The result is shown in FIG. 1. Also, the change in transparence of the device with the passage of time is shown in Table 1 below.

EXAMPLE 3

After dissolving 5 g of a thermoplastic polyester resin (Polyester TP-236, made by Nippon Synthetic Chemical Industry Co., Ltd., glass transition point: 60° C) in 30 ml of methylene chloride, 1 g of a farnesol as a perfume was dissolved therein to provide a homogeneous solution.

The resin solution containing farnesol was coated on a polyethylene terephthalate film having a message "END" printed on the surface thereon at a thickness of 500 μm at room temperature and allowed to evaporate methylene chloride at 40° C. to provide a liquid active substance slow releasing device of this invention containing about 15% by weight the perfume and having a thickness of about 70 μm.

The device was allowed to stand and the remaining amount of the active substance in the device was measured from weight loss of the device. The result obtained is shown in FIG. 1. Also, the change in the transparence of the device with the passage of time is shown in Table 1 below.

COMPARISON EXAMPLE 1

After dissolving 5 g of a thermoplastic polyester resin (Vylon 500, trade nema, made by Toyobo Co., Ltd., glass transition point: 4° C.) in 30 ml of methylene chloride, 1 g of Z-11-tetradecenyl acetate was dissolved therein to provide a homogeneous solution.

The solution was coated on a polyethylene terephthalate film having vapor-deposited aluminum layer at a thickness of 500 μm at room temperature and allowed to evaporate methylene chloride to provide a comparison liquid active substance slow releasing device containing about 15% by weight the attractant and having a thickness of about 70 μm.

The device was allowed to stand at 30° C. and the remaining amount of the active substance in the device was measured from the weight loss of the device. The result is shown in FIG. 1. Also, the change in transparence of the device is shown in Table 1 below.

COMPARISON EXAMPLE 2

After dissolving 5 g of a thermoplastic polysulfon resin (Udel Polysulfon P-1700, trade name, made by Nissan Chemical Industries, Ltd., glass transition point 190° C.) in 30 ml of methylene chloride, 1 g of Z-11-tetradecenyl acetate was dissolved therein to provide a homogeneous solution.

The solution was coated on a polyethylene terephthalate film having vapor-deposited aluminum layer at a thickness of 500 μm at room temperature and allowed evaporate methylene chloride at 40° C. to provide a comparison liquid active substance slow releasing device containing about 15% by weight the attractant and having a thickness of about 70 μm.

The device was allowed to stand in an open atmosphere at 30° C. and the remaining amount of the active substance in the device was measured from the weight loss of the device. The result is shown in FIG. 1. Also, the change in transparence of the device with the passage of time is shown in Table 1 below.

TABLE 1

| | Directly After | After 2 months | After 3 months | After 10 months |
|---|---|---|---|---|
| Example 1 | + | + | + | − |
| Example 2 | + | + | + | − |
| Example 3 | + | + | +~− | − |
| Comparison Example 1 | − | − | − | − |
| Comparison Example 2 | + | + | + | + |

(Note): + means opaque; − means transparency.

It can be seen that by the device of this invention, the resin molding which is initially opaque becomes transparent with the release of the active substance contained it, which shows the end of the release of the active substance.

While the invention has been described in detail and with reference to specific embodiments thereof, it will be apparent to one skilled in the art that various changes and modifications can be made therein without departing from the spirit and scope thereof.

What is claimed is:

1. A liquid active substance slow releasing device comprising a thermoplastic polyester resin having a glass transition point of from 5° C. to 80° C. and an evaporative liquid active substance having a limited solubility for the aforesaid thermoplastic resin, said device being an opaque resin molding of the thermoplastic resin having dispersed therein the liquid active substance as fine droplets in an amount over the saturation solubility and becoming substantially transparent when the amount of the liquid active substance in the resin molding is reduced.

2. The liquid active substance slow releasing device as claimed in claim 1, wherein the resin molding is a sheet or a film.

3. The liquid active substance slow releasing device as claimed in claim 2, wherein the resin molding has a backing composed of a resin sheet, a resin film, a metal foil, a metal vapor-deposited layer, or a laminate thereof on the back surface of the resin molding.

4. A liquid active substance slow release device comprising:
   a thermoplastic polyester resin having a glass transition point of from 5° C. to 80° C., and fine pores of from 0.1–5 microns in size separated from each other by walls of from 0.1–5 microns in thickness; and
   an evaporative liquid active substance having a solubility in the range of 20 parts by weight for said thermoplastic resin, said liquid active substance dispersed in said fine pores of said thermoplastic resin as fine droplets in an amount over the saturation solubility of said thermoplastic resin, said thermoplastic resin becoming substantially transparent when the amount of the liquid active substance in said thermoplastic resin is just below the saturation solubility of said thermoplastic resin.

* * * * *